United States Patent
Kaspar et al.

(10) Patent No.: US 10,751,032 B2
(45) Date of Patent: Aug. 25, 2020

(54) MOISTURE-RESPONSIVE FILMS

(71) Applicant: Transderm, Inc., Santa Cruz, CA (US)

(72) Inventors: Roger L. Kaspar, Santa Cruz, CA (US); Tycho Speaker, Santa Cruz, CA (US)

(73) Assignee: Transderm, Inc., Salt Lake City, UT (US)

( * ) Notice: Subject to any disclaimer, the term of this patent is extended or adjusted under 35 U.S.C. 154(b) by 121 days.

(21) Appl. No.: 15/939,207

(22) Filed: Mar. 28, 2018

(65) Prior Publication Data

US 2018/0345627 A1 Dec. 6, 2018

Related U.S. Application Data

(60) Provisional application No. 62/477,691, filed on Mar. 28, 2017.

(51) Int. Cl.
*A61B 10/00* (2006.01)
*A61B 5/00* (2006.01)
*G01N 33/52* (2006.01)

(52) U.S. Cl.
CPC ........ *A61B 10/0064* (2013.01); *A61B 5/4266* (2013.01); *G01N 33/525* (2013.01); *G01N 33/526* (2013.01); *B32B 2535/00* (2013.01)

(58) Field of Classification Search
CPC .............. A61B 5/4266; A61B 10/0064; G01N 33/525; G01N 33/526
See application file for complete search history.

(56) References Cited

U.S. PATENT DOCUMENTS

| | | | | |
|---|---|---|---|---|
| 2,168,286 | A * | 8/1939 | Warner | D06M 7/00 428/378 |
| 4,190,056 | A * | 2/1980 | Tapper | A61B 5/1172 118/31.5 |
| 8,043,867 | B2 * | 10/2011 | Petruno | G01N 21/8483 436/514 |
| 9,211,248 | B2 | 12/2015 | Dake et al. | |
| 9,918,672 | B2 * | 3/2018 | Kennedy | A61B 5/4266 |
| 2002/0106710 | A1 | 8/2002 | Tuohy et al. | |
| 2005/0287035 | A1 | 12/2005 | Yon-Hin et al. | |
| 2008/0081964 | A1 * | 4/2008 | Zakrzewski | A61B 5/4266 600/306 |
| 2009/0180926 | A1 | 7/2009 | Petruno et al. | |
| 2014/0275862 | A1 | 9/2014 | Kennedy | |

(Continued)

FOREIGN PATENT DOCUMENTS

SU 161371 12/1990

OTHER PUBLICATIONS

International Search Report dated Aug. 23, 2018, in International Application No. PCT/US18/24972, filed Mar. 28, 2018; 15 pages.

(Continued)

*Primary Examiner* — Justin N Olamit
(74) *Attorney, Agent, or Firm* — Nathan S. Smith; Kalpesh V. Upadhye; Morgan, Lewis & Bockius LLP

(57) ABSTRACT

A moisture-responsive film can include a complexing substrate and an iodine layer applied to the complexing substrate to form the moisture-responsive film. The moisture-responsive film can include a test area formed on a testing surface of the moisture-responsive film.

19 Claims, 6 Drawing Sheets

(56) References Cited

U.S. PATENT DOCUMENTS

| | | | |
|---|---|---|---|
| 2017/0231571 A1* | 8/2017 | Rogers | A61B 5/6833 600/301 |
| 2019/0246721 A1* | 8/2019 | Bates | A61B 10/0064 |

OTHER PUBLICATIONS

Russian Office Action from Russian Patent Application No. 2019130477, dated Mar. 11, 2020, 11 pages including English language translation.

* cited by examiner

MOISTURE-RESPONSIVE FILMS

PRIORITY DATA

This application claims the benefit of U.S. Provisional Application Ser. No. 62/477,691, filed Mar. 28, 2017 which is incorporated herein by reference.

BACKGROUND

Hyperhidrosis is a medical condition that causes excessive sweating in one or more areas of the body. For example, excessive sweating can occur on the palms, feet, underarms, and/or head while other areas of the body remain dry. Sweating is normal under certain circumstances, such as when an individual becomes hot or nervous. However, individuals with hyperhidrosis can routinely sweat for no apparent reason. This condition can interfere with a variety of normal daily functions, such as turning a doorknob or using a computer, for example. Further, the excess sweating can soak through the individual's clothing, leading to embarrassment of the individual and/or poor self-image. A number of additional challenges can also be associated with hyperhidrosis.

Figure 1:
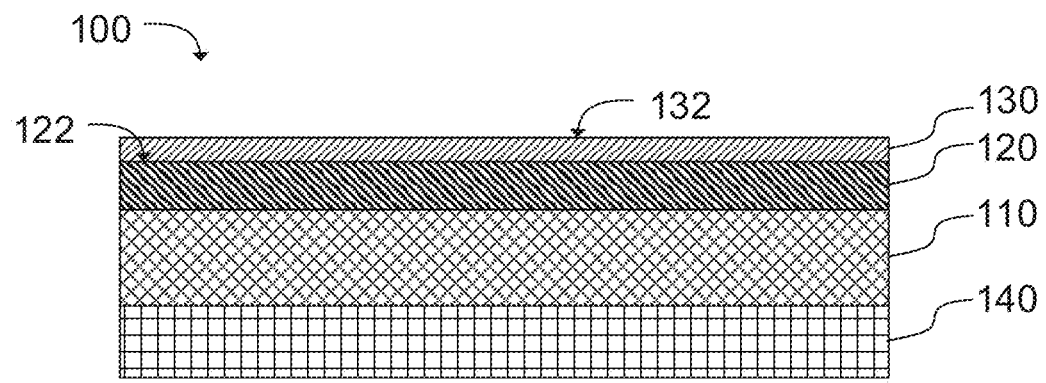
FIG. 1 illustrates a cross-sectional view of a Moisture Responsive Film (MRF), in accordance with examples of the present disclosure.

Reference will now be made to the exemplary embodiments illustrated, and specific language will be used herein to describe the same. It will nevertheless be understood that no limitation of the scope of the invention is thereby intended.

DESCRIPTION OF EXAMPLE EMBODIMENT(S)

Before particular embodiments of the present invention are disclosed and described, it is to be understood that this invention is not limited to the particular process and materials disclosed herein as such may vary to some degree. It is also to be understood that the terminology used herein is used for describing particular embodiments only and is not intended to be limiting.

As used in this written description, the singular forms "a," "an," and "the" shall include express support for plural referents unless the context clearly dictates otherwise.

As used herein, the term "about" is used to provide flexibility to a numerical range endpoint by providing that a given value may be "a little above" or "a little below" the endpoint.

The term "subject" refers to a mammal that may benefit from the administration using a device or method of this invention. Examples of subjects include humans, and other animals such as horses, pigs, cattle, dogs, cats, rabbits, and aquatic mammals.

As used herein, the term "substantially" refers to the complete or nearly complete extent or degree of an action, characteristic, property, state, structure, item, or result. As used herein, sequences, compounds, formulations, delivery mechanisms, or other items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, a "derivative" is a compound obtained from a source compound, an analog, homolog tautomeric form, stereoisomer, polymorph, hydrate, pharmaceutically acceptable salt or pharmaceutically acceptable solvate thereof, by a simple chemical process converting one or more functional groups, by means of oxidation, hydrogenation, alkylation, esterification, halogenation and the like. The term "analog" refers to a compound having a structure similar to that of another one, but differing from it with respect to a certain component. The compound may differ in one or more atoms, functional groups, or substructures, which may be replaced with other atoms, groups, or substructures. In one aspect, such structures possess at least the same or a similar therapeutic efficacy for a given indication. The term "tautomer" or "tautomeric form" refers to structural isomers of different energies which are interconvertible via a low energy barrier. The term "stereoisomer" refers to one of a set of isomers whose molecules have the same number and kind of atoms bonded to each other, but which differ in the way these atoms are arranged in space. The term "polymorph" refers to crystallographically-distinct forms of a substance. In addition, an agent can be said to be "derived" from a source containing many compounds or agents, such as a plant, fungus, bacteria, or other organism. In this context, the agent can be described or otherwise referred to in terms of its source, rather than by its own properties, characteristics, name, or attributes per se. For example, an extract obtained from a plant may be described as "derived" from the plant. Further, in some examples, the derivative can be more or less potent than the source compound and/or can be more or less toxic than the source compound. In some specific examples, the derivative can be less potent and/or less toxic than the source compound.

As used herein, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the composition's nature or characteristics would be permissible if present under the "consisting essentially of" language, even though not expressly recited in a list of items following such terminology. When using an open ended term in the written description, like "comprising" or "including," it is understood that direct support should be afforded also to "consisting essentially of" language as well as "consisting of" language as if stated explicitly and vice versa.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.5 to 10 g" should be interpreted to include not only the explicitly recited values of about 0.5 g to about 10.0 g, but also include individual values and sub-ranges within the indicated range. Thus, included in this numerical range are individual values such as 2, 5, and 7, and sub-ranges such as from 2 to 8, 4 to 6, etc. This same principle applies to ranges reciting only one numerical value. Furthermore, such an interpretation should apply regardless of the breadth of the range or the characteristics being described.

Unless otherwise defined, all technical and scientific terms used herein have the same meaning as commonly understood to one of ordinary skill in the art to which this invention belongs. Although any methods, devices and materials similar or equivalent to those described herein can be used in the practice or testing of the invention, representative methods, devices, and materials are described below.

It is noted that when discussing the devices, systems, and associated methods, each of these discussions can be considered applicable to each of these embodiments, whether or not they are explicitly discussed in the context of that embodiment. Thus, for example, in discussing a moisture-responsive film (MRF), such an MRF can also be used in a diagnostic method, and vice versa. With this in mind, MRFs and associated methods will be discussed in further detail.

One method used to determine sweat quantity in a clinical diagnostic setting is the starch/iodine test, in which the area of the patient to be tested is painted with an iodine solution, and then coated with either dry starch or a suspension of starch in a non-aqueous medium such as mineral oil. However, the existing starch/iodine test is burdensome, time-consuming, and unpleasant, leaving the patient stained with iodine and dark purple iodine/starch complex, even after gummy starch and/or oily residue has been cleaned off. Patients with hyperhidrosis may already present with poor self-image and embarrassment, which may make skin staining more traumatic. Further, the determination of the degree of sweating can be highly subjective as to what constitutes hyperhidrosis. Typically, documentation of the test requires photographing the patient's exposed skin, which may be influenced by camera focus and ambient lighting during the photograph, leading to further inaccuracy and encumbering comparison to previous tests. In many cases the burdensome test may be bypassed altogether and diagnosis may be made on subjective (non-quantitative) physician assessment or based upon even more subjective patient self-assessment, potentially leading to over-diagnosis and poor resource utilization. Thus, a need exists for a simple, quantitative test to identify and grade hyperhidrosis in a clinical setting.

The present disclosure describes alternative diagnostic tools and associated methods having adequate performance from only brief contact with the skin to be tested, that leave no stain or residue upon the tested skin area, and that can be electronically scanned in a highly reproducible fashion. Further, image analysis of the color intensity of the test area, as compared to a calibration region or standard score, can produce an objective, quantified result that is readily compared to previous or future tests. Thus, the present tools and methods can save the patient discomfort, can reduce time burdens on the administering physician or staff, and can produce a more reliable quantified result than the current standard of care.

In accordance with this, an MRF for use as a diagnostic tool is described herein. Further, the present disclosure also provides a method of diagnosing or detecting hyperhidrosis, or other abnormal sweating condition, and/or monitoring a reduction in sweat production using an MRF.

In further detail, in some examples, the MRF can include a complexing material that forms a visualizable complex in the presence of iodine and water, for example by development of a visible color. Non-limiting examples of complexing materials that can form such visualizable complexes can include a starch, polyvinyl alcohol, the like, or a combination thereof. Where reference is made to starch, it is to be understood that any complexing material that forms such visualizable complexes may be substituted for the starch in the compositions, systems, and methods disclosed herein. In some examples, the MRF can include a complexing substrate, such as a starch-containing substrate, that forms a visualizable complex in the presence of iodine and water and a thin layer of iodine applied to the complexing substrate.

Generally, the complexing substrate can include a variety of substrate materials. Without limitation, substrate materials can include paper, fabric, polymeric materials, the like, or combinations thereof. In some other examples, the substrate material can be a rigid material or a coating on a rigid material. In some specific examples, the substrate material can be a cellulose or paper-based material. In some further examples, the starch or other complexing material can be combined with the raw materials used to prepare the cellulose or paper-based material to provide the paper-based material with increased dry strength and/or a modified surface texture. Thus, in some examples the starch or other complexing material can be mixed throughout the paper-based material. In additional examples, the starch or other complexing material can be included as a surface coating applied to the paper-based material to provide the complexing substrate with a complexing surface. Where a coating is applied to the paper-based material, the coating can be any suitable coating that can have any suitable combination of ingredients. For example, the coating can include any suitable combination of pigments, binders (e.g. acrylic binders, latex binders, etc.), polymeric materials (e.g. those described elsewhere herein), fillers (e.g. calcium carbonate, kaolin, talc, titanium dioxide, etc.), plasticizers (e.g. propylene glycol, glycerol, sorbitol, polyethylene glycol, other polyols, other polyethers, etc.), the like, or a combination thereof.

In some examples, the substrate material can be made of or include a fabric material. A variety of suitable fabric materials can be employed to prepare the complexing substrate. Non-limiting examples can include cotton, linen, silk, hemp, bamboo, polyamides, polyesters, polyurethanes, the like, or a combination thereof. In some examples, it can be desirable to use a water-absorbent fabric (e.g. cotton, linen, silk, hemp, bamboo, the like, or a combination thereof) to prepare the complexing substrate. In some other examples, it can be desirable to use a water-resistant fabric (e.g. polyamides, polyesters, polyurethanes, the like, or a combination thereof) to prepare the complexing substrate. In some additional examples, it can be desirable to use a combination of a water-absorbent fibers and water-resistant fibers to prepare a blended fabric for use in preparing the complexing substrate. In some examples, starch or other complexing material can be included as a surface coating applied to the fabric material to prepare a complexing surface. Where a coating is applied to the fabric material, the coating can be any suitable coating that can have any suitable combination of ingredients, such as those described above, for example. In some examples, the fabric material can be soaked in a complexing material medium, or the like, to deposit a suitable amount of starch or other complexing material on a surface of the fabric material. Other suitable methods of applying a complexing material to the fabric material can also be used.

In additional examples, the substrate material can be made of or include a polymeric or other suitable material. Non-limiting examples of such materials can include polyvinyl alcohol, polyvinylpyrrolidone, carbomers, polyacrylic acid, polyoxyethylene/polyoxypropylene copolymers, other copolymers, albumins, casein, zein, collagen, other proteins, glucose, sucrose, maltose, trehalose, amylose, dextrose, fructose, mannose, galactose, other sugars, erythritol, threitol, arabitol, xylitol, ribitol, mannitol, sorbitol, galactitol, fucitol, iditol, inositol, volemitol, isomalt, maltitol, lactitol, maltotriitol, maltotetraitol, polyglycitol, other sugar alcohols, chondroitin and/or other glycosaminoglycans, inulin, starches, acacia gum, agar, carboxymethyl cellulose, methyl cellulose, ethyl cellulose, alginates, carrageenan, cassia gums, cellulose gums, chitin, chitosan, curdlan, gelatin, dextran, fibrin, fulcelleran, gellan gum, ghatti gum, guar gum, tragacanth, karaya gum, locust bean gum, pectin, starch, tara gum, xanthan gum, and other polysaccharides, and functionalized derivatives of any of the above, copolymers thereof, or mixtures thereof.

Where the substrate material is made of or includes a polymeric or other suitable material, starch or other complexing material can be applied to the substrate material in a variety of ways. In some examples, starch or other complexing material can be applied to the polymeric material or other suitable material as a surface coating to form a complexing surface. Where this is the case, the surface coating can include any suitable combination of ingredients, such as those described above, for example. In yet other examples, starch or other complexing material can be combined with the raw materials used to prepare the polymeric or other suitable material. Thus, starch or other complexing material can be dispersed throughout the complexing substrate. In some examples, the polymeric or other suitable material can be soaked and/or swollen in a complexing material medium to apply an adequate amount of complexing material to the polymeric or other suitable material to form the complexing substrate. Other suitable methods of applying a complexing material to the polymeric or other suitable material can also be used.

As such, a variety of substrate materials can be used to prepare the complexing substrate. In some examples, the composition of the complexing substrate is generally only limited by the ability to prepare a solution containing dissolved or dispersed starch that can be dried to form a film that includes or otherwise incorporates the complexing material dispersed uniformly throughout the film. In other examples, the complexing substrate can incorporate starch or other complexing material within and/or throughout the complexing substrate.

Where starch is used as the complexing material, a variety of different starches can be used to make the complexing substrate (e.g. via coating, mixing, etc.). In some examples, the starch can include a native starch, such as corn starch, maize starch, potato starch, rice starch, tapioca starch, wheat starch, the like, or a combination thereof. In some examples, the starch can be a modified starch, such as oxidized starch, cationic starch, amphoteric starch, esterified starch, enzymatically denatured starch, the like, or a combination thereof. In some examples, the starch can include a combination of a native starch and a modified starch. Generally, any starch or starch derivative can be used that can form a colored complex with iodine in the presence of water. In some specific examples, the complexing substrate can include at least 0.75 nanograms (ng) starch (or other complexing material)/millimeter squared ($mm^2$) surface area, at least 1 ng starch (or other complexing material)/$mm^2$ surface area, at least 2 ng starch (or other complexing material)/$mm^2$ surface area, or at least 5 ng starch (or other complexing material)/$mm^2$ surface area.

As one specific, non-limiting example, a complexing substrate can be formed by preparing an aqueous solution containing 15% polyvinyl alcohol (Spectrum Chemicals, New Brunswick, N.J.) and 1% maltodextrin (Maltrin M040, Grain Processing Corporation, Muscatine, Iowa), subsequently casting or otherwise spreading the solution into a 200 μm thick film, and evaporating to dryness. The resulting film can be coated with iodine, as described below, to form an MRF.

In further detail, a thin layer of iodine ($I_2$) can be applied to the complexing substrate. The iodine layer can be applied to the complexing substrate in a variety of ways. In some examples, the complexing substrate can be coated with iodine without triggering strong color formation by coating with a non-aqueous iodine solution (such as a solution of iodine containing less than 5 wt % water, 2 wt % water, 1 wt % water, or 0.5 wt % water) and subsequent evaporation. A variety of non-aqueous solvents can be used to prepare a non-aqueous iodine solution. Non-limiting examples can include methanol, ethanol, n-hexane, ethyl acetate, chloroform, diethyl ether, the like, or a combination thereof. As one specific example, a solution of 1% iodine in reagent ethanol (Spectrum Chemicals, New Brunswick, N.J.) can be sprayed onto the maltodextrin/PVA film described above and evaporated to dryness. The resulting iodine coated starch/PVA film can produce a strongly colored complex in the presence of sub-microliter quantities of water. If water exposure is spatially discontinuous, such as when the film is pressed against skin and individual sweat ducts are distributed over different areas of the skin surface, a 2-dimensional image will result from the localized hydration of the film in the region of those sweat ducts.

In other examples, iodine can be deposited on the complexing substrate without producing the strongly colored complex by direct condensation of iodine vapor in the absence of liquid water. For example, a paper-based material, a fabric material, a polymeric material, or other suitable substrate material can be used to prepare a complexing substrate as described herein, and iodine can be directly condensed to the complexing substrate. In some examples, thermal cash register paper (Thermal Paper Direct Inc, Mahwah, N.J.) or other suitable paper-based materials, or other suitable substrate material for the complexing substrate can have useful quantities of starch for preparation of the MRF. Further, as non-limiting examples of specific paper-based substrates, commercial copy paper, inkjet printer paper, laser printer paper, and multipurpose office paper tested from multiple national brands including Boise (Paper Corporation of America (Lake Forest, Ill.), Hammermill Paper (Erie, Pa.), HP (Palo Alto, Calif.), Weyerhaeuser (Seattle, Wash.), Xerox (Norwalk, Conn.), or the like can include useful levels of starch content when prepared as described herein. Thus, most sources of commercial printer or writing paper is typically useful for the purposes of preparing an MRF as described herein. As one specific example, the MRF can be prepared by placing a sample of Hammermill Premium Multi-Purpose paper in a glass container with crystalline iodine at 24° C. Over the course of several hours the paper can develop a light brown tint due to iodine vapor condensation onto the paper surface. The resulting MRF can develop a strong purple color with application of moisture and can readily produce a fingerprint image including darkened spots at the site of active sweat pores. Depending upon the relative moisture of the fingers of the tested individual this image may appear in as little as 5 seconds or may take as long as 5 minutes to appear clearly. In other aspects, a longer or shorter contact time may be more optimal to detect a particular moisture level or tissue feature and no specific time requirement is implied herein. In some examples, iodine evaporation and subsequent transfer to a complexing substrate can be accelerated by heating the floor of the glass container to a temperature greater than 24° C., such as greater than or equal to 40° C., 50° C., 60° C., 70° C., or other elevated temperature.

In yet other examples, the iodine layer can be applied to the complexing substrate by bringing an iodine coating layer or iodine-rich layer into direct physical contact with the complexing substrate. In some cases, the iodine coating layer or iodine-rich layer can be adhered to or otherwise transferred to the complexing substrate to form the iodine layer. In some further examples, the iodine coating layer can include a binder (e.g. acrylic binders, latex binders, the like, or a combination thereof), a filler (e.g. calcium carbonate, kaolin, talc, titanium dioxide, the like, or a combination thereof), a plasticizer (e.g. propylene glycol, glycerol, sorbitol, polyethylene glycol, other polyols, other polyethers, the like, or a combination thereof), a polymeric material (e.g. those listed herein), the like, or a combination thereof. For example, a thin layer of sodium alginate (Manucol DH, FMC Biopolymers, Philadelphia, Pa.) can be produced by drying a 2% solution of the alginate further containing 0.05% glycerin (Spectrum Chemicals, New Brunswick, N.J.) as a plasticizer, and 1% iodine (Spectrum Chemicals) on a polymethylmethacrylate (PMMA) sheet substrate. Alginate alone does not produce a colored complex with iodine. The dried alginate film containing iodine can be peeled from the PMMA substrate and applied to one of the complexing substrates described above. The resulting 2-layer or bi-layer MRF can form a strongly colored starch iodine complex locally when a drop of water is applied.

The thin iodine layer can provide an even, brown color on the surface of the complexing substrate. This color can be retained for several weeks when stored in a closed, air-tight container. Such containers can include glass, polyethylene, wax, aluminum foil, the like, or combinations thereof. However, some metals and other materials, notably iron-containing materials, are sensitive to iodine and rapidly corrode, and are therefore not ideal for storage of the iodine-rich films unless provided with a protective overcoating impermeable to iodine vapor. When the thin iodine layer is exposed to moisture, such as from a fingerprint, hand print, foot print, or other skin surface (e.g. an axillary skin surface, a chest skin surface, a groin skin surface, etc.), and associated sweat ducts, the moistened area darkens substantially. Further, in some examples, this darkening can be substantially irreversible, such that when the imprinted and darkened area is left exposed to air, it remains darkened. In contrast, in some examples, the undarkened areas can lighten over time when exposed to air until the brown color is substantially or completely dissipated. Without wishing to be bound by theory, it is believed that this can result from iodine in the presence of water becoming entrapped in the helices of amylose or other complexing material in the complexing substrate. This entrapped form of the iodine can be less labile and less subject to loss via evaporation. The evaporation of the non-imprinted areas also serves to increase the contrast of the imprinted areas, making imaging of the imprinted MRF clearer.

It is noted that by applying the iodine layer to the complexing substrate, there is no need to apply iodine to the skin surface prior to contacting the skin surface with the MRF. This can provide a more uniform measurement across the MRF as compared to applying iodine to the skin surface and then contacting the skin surface to the complexing substrate. However, the complexing substrates can be used without an incorporated iodine layer. In these examples, the skin or other skin surface can be pre-coated with iodine and then brought into contact with the complexing substrate to produce images similar to those produced by the MRF. In some examples, the MRF can be embodied in a thin, flexible form that can conform to a non-planar surface. In some embodiments the MRF can also comprise an elastically deformable matrix such as a stretchable film or a resilient foam backing such that non-planar surfaces can be maximally contacted.

In some additional examples, the MRF can include a backing layer applied to the back side of the complexing substrate, the back side being opposite the side of the complexing substrate to which the iodine layer is applied. In some examples, the backing layer can provide increased sensitivity in detecting moisture content on a skin surface. In some examples, this can result from greater confinement of the moisture within the MRF rather than allowing the moisture to pass through the MRF. Thus, the backing layer can provide a selectable degree of moisture permeability. For example, in some cases, the backing layer can be a water-impermeable layer. In yet other examples, the backing layer can be a semi-impermeable layer with respect to water. In yet other examples, the backing layer can be a water absorbent material. These different types of backing layers can accommodate different levels of skin moisture. For example, a highly absorbent backing layer can be more suitable for a high moisture sample without overexposing or saturating the signal of the MRF. Conversely, a highly impermeable backing layer can provide increased sensitivity for low moisture samples by preventing the moisture from passing through the MRF.

FIG. 1 illustrates a cross-sectional view of one example of an MRF 100. The MRF 100 can include a substrate material 110 and a complexing material coating 120 applied to a surface thereof. In this particular example, substrate material 110 and starch-containing coating 120 can form the complexing substrate and the complexing material coating 120 can form a complexing surface 122 of the complexing substrate. In other examples, starch or other complexing material may be dispersed throughout substrate material 110. Where this is the case, it may not be necessary to include complexing material coating 120, depending on the concentration of the complexing material on the surface of the substrate material 110. Where this is the case, the complexing surface can be a surface of the complexing substrate to which an iodine layer 130 is applied. In this particular example, an iodine layer 130 is applied to the complexing material coating 120 to form a testing surface 132. In some examples, a backing layer 140 can be applied to the complexing substrate on a side opposite to a side to which the iodine layer 130 is applied or opposite the testing surface 132. It is noted that the various features of the drawing are not intended to be drawn to scale and are represented merely to facilitate description of an example of an MRF.

When used as a diagnostic tool, the MRF can be further treated with at least one preselected dose of water so as to produce at least one calibrated color response, or mark, in a preselected area or areas of the MRF, such as in a corner area or along an edge, leaving an untreated area that can be used to make a test measurement. In some examples, the calibration mark(s) or calibration area can be preselected to indicate a threshold color, where coloration generated in the test area can be weaker than, similar to, or stronger than the calibration mark(s), indicating the presence or absence of a diagnostically relevant moisture level. In other examples, the calibration area can be preselected to indicate a severity or degree of a diagnostically relevant moisture level. Where this is the case, a plurality of calibration marks can be employed, each calibration mark representing a different moisture level. The coloration generated in the test area can be compared to the calibration marks to determine a severity or degree of a diagnostically relevant moisture level.

Figure 2A:
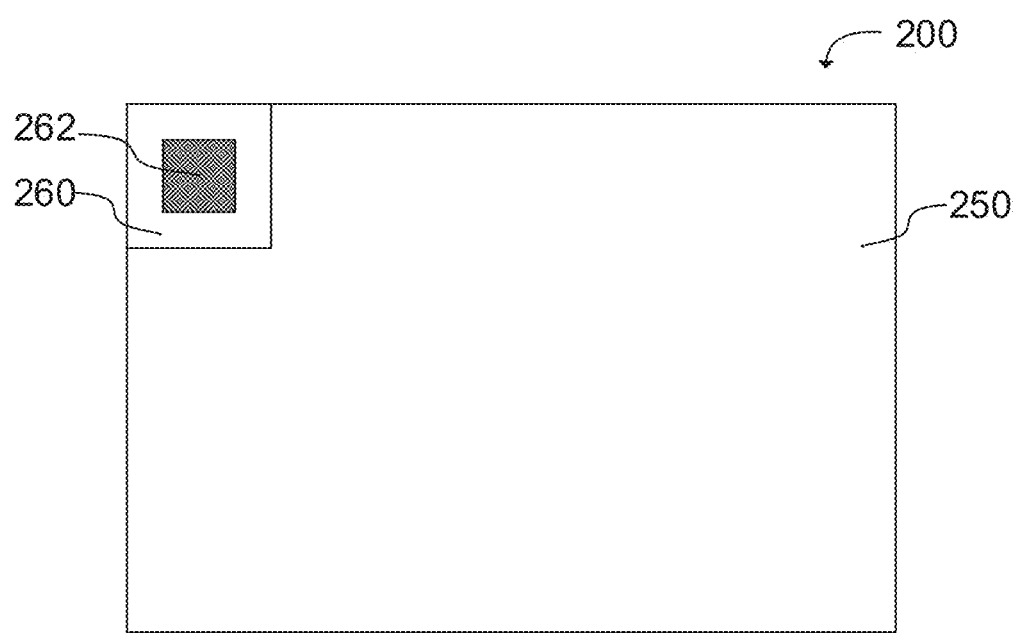
FIG. 2A illustrates a plan view of an MRF, in accordance with examples of the present disclosure.

FIG. 2A illustrates one specific example of an MRF 200 having a test area 250 and a calibration area 260 with a single threshold calibration mark 262. Thus, coloration generated in the test area 250 can be compared to the threshold calibration mark 262 in the calibration area 260 to determine the presence or absence or a diagnostically relevant moisture level. In other examples, the calibration can extend along a portion of or an entire edge of the MRF and can include a plurality of calibration marks or a gradient calibration mark to determine a degree of a diagnostically relevant moisture level.

In one example, the calibration mark(s) can be produced by direct application of water. In another example, the calibration mark(s) can be produced by application of a non-aqueous material in which water is dispersed, dissolved, or entrapped. As one non-limiting example, this can be accomplished by applying a preselected quantity of water dissolved in a preselected quantity of anhydrous ethanol to the calibration area. In another example, a plastic sponge loaded with a preselected quantity of water can be applied to the MRF calibration area. In yet another example, the calibration mark(s) can be produced by exposing the calibration area to a stream or atmosphere having a preselected concentration of water vapor, such as in air or other suitable fluid, for a preselected time to develop the appropriate calibration reference color. In another example, the calibration mark(s) can be produced by locally cooling the calibration area to a preselected temperature for a preselected time chosen to produce condensation of ambient moisture sufficient to form the mark.

In other examples, the MRF calibration mark(s) can be replaced by a mark or marks on a separate calibration strip or calibration key that are printed in ink. The printed mark(s) of the separate calibration strip can correspond to the color generated by adding a preselected quantity of moisture to an area of the MRF. In some examples, the calibration strip or calibration key can include a threshold color, where coloration generated on the MRF can be weaker than, similar to, or stronger than the threshold calibration mark, indicating the presence or absence of a diagnostically relevant moisture level. In other examples, the calibration strip or calibration key can include a plurality of calibration marks or a calibration mark having a continuous or semi-continuous color gradient indicating a severity or degree of a diagnostically relevant moisture level based on the coloration generated on the MRF.

Figure 2B:
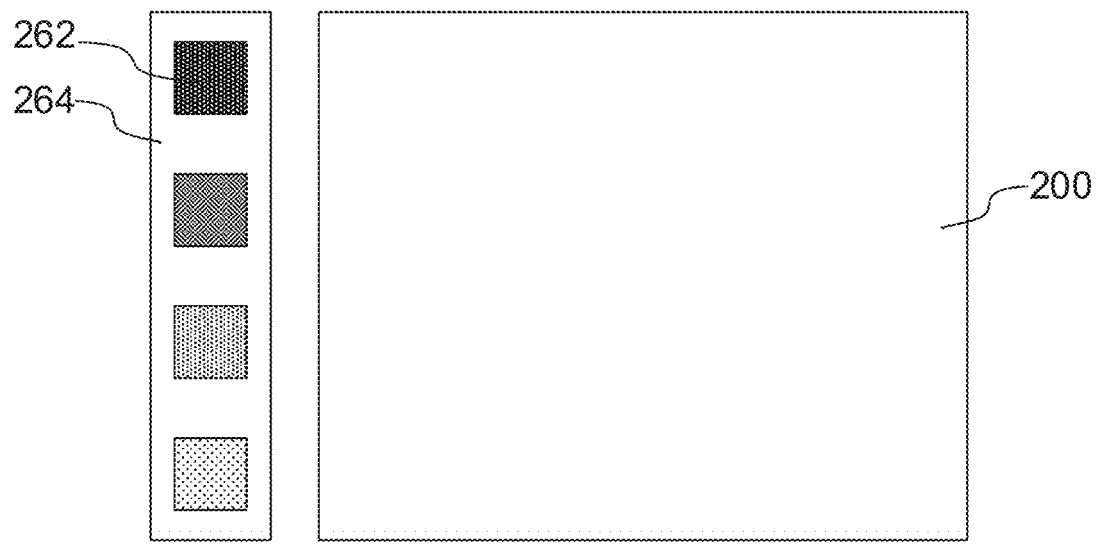
FIG. 2B illustrates a plan view of an MRF and a separate calibration strip, in accordance with examples of the present disclosure.

FIG. 2B illustrates one example of an MRF 200 where the entire surface of the MRF is the test area. FIG. 2B further illustrates a separate calibration strip 264 that includes a plurality of calibration marks 262. In this particular example, a single calibration strip 264 can be placed adjacent to MRF 200 to compare a degree of coloration generated on the MRF to the plurality of calibration marks to determine a severity or degree of a diagnostically relevant moisture level.

In yet other examples, the function of the calibration mark can be reproduced in software, to which the test area coloration can be electronically compared. However, in some examples, where the calibration mark is reproduced in software, the MRF can include a control standard area that can be used to normalize the data acquisition and analysis via the software. In some examples, the control standard area can be prepared by printing a specific color standard area with ink. In other examples, the control standard area can be prepared by applying a predetermined amount of water to the control standard area. In yet other examples, a control standard area can be unnecessary and the software can determine a presence or absence or a degree of a diagnostically relevant moisture level based on electronic or stored calibration information.

Thus, the calibration area of the MRF can be produced or generated in a number of suitable ways. The manner in which the calibration area is produced or generated is not particularly limited and any suitable method can be used.

With a suitable calibration area associated with the diagnostic MRF and/or associated method, a medical patient with possible hyperhidrosis, or other sweating or moisture-related condition, can place the area of skin to be diagnosed in contact with the moisture-responsive test area of the MRF diagnostic tool. A variety of skin surfaces can be used for testing, such as a palm, the bottom of the foot, the face, the chest, the axillary region, the groin, or other suitable skin surface. The tested skin surface can remain in contact with the MRF for a preselected period of time, after which the skin surface can be removed from contact with the MRF to permit visual inspection of the coloration developed in response to moisture from perspiration on the patient's skin surface. The skin surface can remain in contact with the moisture-responsive test area for a variety of predetermined times, depending on the particular calibration criteria selected, type of MRF used, and the like. Non-limiting examples of application time periods can include a time period from about 1 second to about 300 seconds, about 2 seconds to about 240 seconds, about 3 seconds to about 120 seconds, about 5 seconds to about 90 seconds, about 8 seconds to about 60 seconds, or about 10 seconds to about 30 seconds.

It is noted that sweating is a natural biological process and there are a number of factors that can induce sweating. Therefore, it can be desirable to take measures to minimize false positives or to maximize the accuracy of the measurements. For example, in some cases, a test subject can become nervous or anxious prior to performing the test, which can induce sweating and possibly produce an erroneous test result. As such, in some cases, a number of pre-test procedures can be performed to help minimize erroneous test results. For example, in some cases, a test subject can be instructed to dry the skin surface to be tested with a towel, an electric dryer, the like, or a combination thereof prior to performing the test. In some examples, the test subject can be instructed to dry the skin surface to be tested at least or about 3 minutes, at least or about 5 minutes, at least or about 8 minutes, at least or about 10 minutes, or at least or about 15 minutes prior to performing the test. In some examples, the test subject can be instructed to dry the skin surface to be tested at a time within a range of from about 5 minutes to about 30 minutes, or from about 10 minutes to about 60 minutes, prior to applying a skin surface to the test area, or other suitable timeframe. In some further examples, it can be desirable to control the environment in which the test is performed. For example, in some cases, it can be desirable to perform the test in an environment having a controlled temperature, humidity level, air flow, the like, or a combination thereof. In some examples, the test subject can be instructed to remain within the controlled test environment for a predetermined period of time prior to performing the diagnostic test. In some further examples, the test subject can be instructed to dry the skin surface to be tested while the test subject is within the controlled test environment and wait a predetermined period of time prior to applying the skin surface to the MRF for a predetermined period of time. In some further examples, a heart-rate of the test subject can be monitored prior to performing the test to verify that the test subject's heart rate is within a predetermined range (e.g. from about 60 beats per minute to about 100 beats per minute, or less than or equal to 100 beats per minute). Various other pre-test procedures can also be performed. Thus, one or more pre-test procedures, such as the pre-test procedures described above, can be followed to minimize erroneous test results.

Optionally, after the test is performed, the MRF can be electronically imaged, such as with a flatbed document scanner, a camera from a portable computer or smartphone, other suitable electronic imaging technology, or a combination thereof. In some examples, the electronically scanned image can optionally be analyzed using generic image analysis software, such as NIH ImageJ open-source software, or by a corresponding program or application running on a computer or smartphone. In some additional examples, the image can be acquired as part of the analysis program or application, which performs the color density comparison between the test area and the calibration area, determining whether the moisture in the test area is above, below, or similar the level in the calibrated area, such that a diagnostic result may be directly determined.

Further, in some examples, the MRF can also be imprinted with tracking codes, electronic scan patterns, text, instructions, and/or areas to be written in, as part of a form document or the like. In such examples, the test area can be a subsection of the form document. In some examples, before and/or after testing, the area of the MRF to be used for testing can be protected from water exposure or loss of iodine, such as by sublimation, by a protective film, covering, or packaging. In some additional examples, the testing area can be adjacent to or continuous with the calibration area, facilitating comparison of the color signal from moisture in the test area with that of the calibration area.

Thus, as previously mentioned, the MRF can be used in a method of diagnosing or detecting hyperhidrosis, or other moisture-related condition, and/or monitoring a reduction in sweating or moisture content on a skin surface. The method can include providing an MRF to a subject having a moisture-responsive test area, and optionally a calibration area. The method can further include applying a skin surface of the subject to the test area of the MRF for a predetermined period of time and subsequently removing the skin surface from the test area to reveal an exposed test area. In some examples, the skin surface can be any skin surface where it is desirable to determine sweat production or skin surface moisture levels for any reason. In some specific examples, the skin surface can be the skin surface of a foot, such as the bottom of a foot, or of a hand, such as the palm of a hand, an axillary region (e.g. armpits), a chest region, a groin region, a face region, or other suitable skin surface.

As described above, the MRF can become darkened upon exposure to skin moisture. Thus, when the test area of the MRF is contacted with a sample skin surface, the MRF will darken in proportion to the moisture content of different areas of the skin surface. Thus, the exposed test area can provide a "fingerprint" or "perspirograph" of the sample skin surface. The exposed test area can be compared to a calibration area associated with the MRF, such as a calibration area located on the MRF, a calibration area on a separate calibration strip or calibration key, or an electronic calibration area, to determine whether the subject has hyperhidrosis, or other moisture-related condition. Further, the exposed test area can be used for monitoring of sweat production over time. In some examples, sweat production can be ameliorated by treatment with a therapeutic agent. Thus, monitoring the condition with an MRF can help verify that a therapeutically effective amount of the therapeutic agent is being administered to the subject. As such, this method can be performed at any suitable interval to monitor the progress of treatments. It is also noted that it can be desirable to perform a number of measurements over a predetermined period of time to determine average scores. This can help minimize erroneous data due to an anomalous data point due to external factors, such as anxiety, elevated heart rate, etc. Thus, in some cases, an average of a number of test results can be monitored over time to monitor the progress of treatments.

When the MRF is suitably exposed to moisture by contact with a finger, palm, toe, foot, or other suitable skin surface, the moisture content of the contacted skin as well as individual sweat ducts is recorded in a distinctive pattern, similar to well-known ink-based fingerprint recording. However, the MRF records both the skin contact area and evidence of active sweat production at the duct outlets. This combined pattern is unique to individuals in the same manner as ink-based or other fingerprint information. It is well understood that by use of silicone or other polymeric impressions, ink-based or oil-based fingerprints can be replicated with high reproducibility, even to circumvent fingerprint-based security measures. In contrast, the presence of active sweat ducts distributed within the fingerprint produced by the MRF technology can be very difficult to reproduce, and thus can provide a much higher level of security in such identifying records.

While the MRF diagnostic tool and associated methods have generally been described with reference to diagnosing and monitoring sweat production or other moisture related conditions associated with a skin surface, the MRF and associated methods are not limited to such examples. For example, the test area of the MRF can be exposed to a stream of a gas containing water vapor, or human breath, to determine the presence or level of water in the gas or to determine whether a person is breathing. In yet other examples, the water content of a cut plant or fruit can be tested. In another example, the wide, flat dimensions of the MRF can be covered or coated with an impermeable layer, such that ingress of moisture comes from exposure of the edge. In a further example, the MRF can produce an irreversible indication of water exposure in protective packaging or shipment monitoring or other uses. In another example, the MRF can be incorporated into an electronic device to disclose exposure to water that might damage the device. In another example, the MRF can take the form of a small test strip inserted into a moisture meter. Thus, the MRF and associated methods can be used with any suitable method where water determination is desirable. Further, the MRFs as described herein can provide a simple, quantifiable, and reproducible means of determining the amount of water present on a test surface, and is physically flexible, permitting contact with irregularly shaped surfaces.

Thus, the present disclosure also describes methods of identifying surface features based on moisture content at the surface. Generally, the methods can include applying a surface to a test area of a moisture-responsive film (MRF) as described herein for a predetermined period of time and removing the surface from the test area to reveal an exposed test area. As described herein, the surface can include a plant surface, a fruit surface, a packaging surface, a surface of an electronic device or component, or the like. In still other examples, the surface can include a skin surface of a subject.

Where the surface is a skin surface, a variety of surface features can be determined based on moisture content. For example, in some cases, the methods can be used for fingerprinting or other identification methods based on location of sweat ducts. Where this is the case, the MRF may include one or more test areas to accommodate one or more skin surface locations, such as fingertips, for example.

Figure 2C:
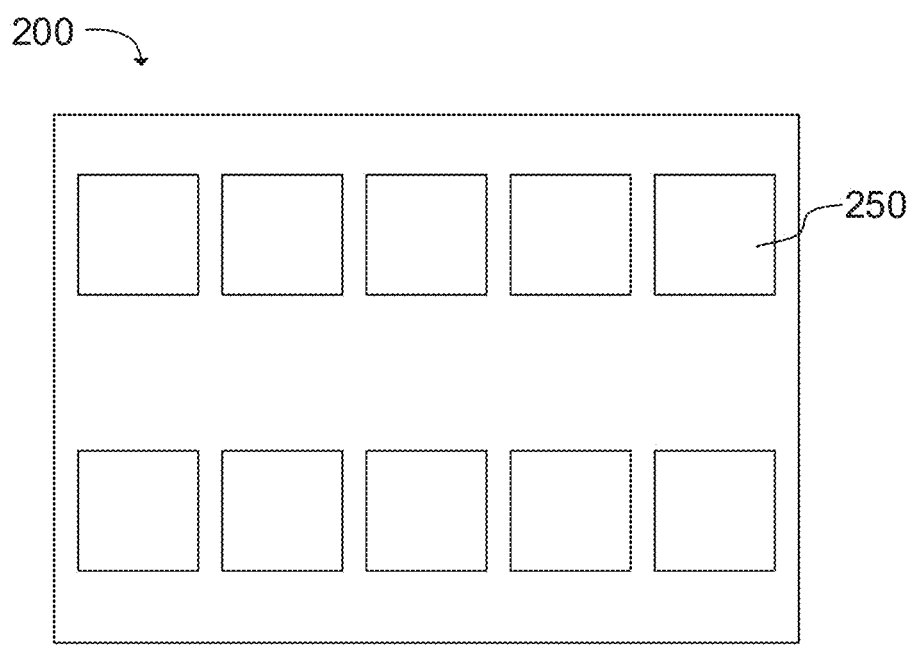
FIG. 2C illustrates a plan view of an MRF, in accordance with examples of the present disclosure.

For example, FIG. 2C illustrates an MRF 200 that includes a plurality of test areas 250. MRFs with a plurality of test areas can be effective at assessing or identifying surface features of a plurality of surfaces, such as for fingerprinting purposes, for example. In other examples, an MRF having a plurality of test areas can be used to collect moisture data about a common surface, such as a skin surface, numerous times to generate a broader profile of the surface, to acquire additional data points to generate average test scores regarding the common surface, or the like, for example. While the MRF in FIG. 2C does not include a calibration area, in some examples it can still be valuable to compare surface features to one or more calibration marks to determine a significance or relevance of a particular result.

The present disclosure also describes a moisture-responsive film (MRF) system or kit. The system or kit can include one or more MRFs as described herein. In some examples, the MRF of the system or kit can include a calibration area. Where this is the case, in some examples, the system can include one or more water standards that can be applied to the calibration area to generate the colored calibration mark(s). Where this is the case, the water standards can be applied to the calibration area via a dropper, a pipette, or other suitable dispensing apparatus. In some examples, the dispensing apparatus can be included in the system or kit. In other examples, the system can include instructions regarding how to prepare one or more water standards and how to apply the water standard(s) to the calibration area. In still other examples, the calibration area can be printed with ink or similarly formed to prepare the colored calibration mark(s).

In some examples, the MRF may not include a calibration area. In some examples, the system can include one or more separate calibration strips or keys having a calibration mark or scale printed or otherwise formed thereon. In some cases, the calibration strip or key can include one or more designated calibration areas to which a water standard can be applied to generate the calibration mark(s). Where this is the case, one or more water standards can be included in the system or kit for use with the calibration strip(s) or key(s).

In other examples, the system or kit can include instructions regarding how to use the MRF in connection with electronic calibration data via software. Where this is the case, the MRF may not include a calibration area. Further, in some examples, the system or kit may not include a calibration strip or key, a water standard, or any other non-electronic calibration tools.

The system or kit can also include instructions regarding how to use the system or kit. For example, the instructions can direct an end user to apply an MRF to a skin surface for a predetermined period of time. In some examples, the instructions can direct an end user how to generate appropriate color calibration data for comparison with the test results. In still other examples, the instructions can direct an end user to perform one or more pre-test procedures prior to performing the test.

In some examples, the kit can also include a suitable skin drying material to prepare the test site for application of the MRF. In some examples, the skin drying material can include a water-absorbent fabric (e.g as those described herein). In some examples, the water absorbent fabric can be a microfiber fabric. In some examples, the skin drying material can include a paper-based towel, a disposable towelette including a drying solvent (e.g. ethanol, isopropyl alcohol, etc.), or the like. Any combination of these skin drying materials, or other suitable skin drying materials, can be included in the system or kit.

A few non-limiting examples are provided below to help illustrate a few of the benefits of the methods, devices, and systems disclosed herein. These examples are provided for illustrative purposes only and are not intended to be limiting.

In some examples, a moisture-responsive film can include:

a complexing substrate containing a complexing material that forms a visualizable complex in the presence of iodine and water; and an iodine layer applied to the complexing substrate to form a moisture-responsive film including a test area.

In some examples, the complexing substrate comprises paper, fabric, a polymeric material, or a combination thereof.

In some examples, the complexing substrate comprises paper.

In some examples, the complexing material is mixed throughout the paper.

In some examples, the paper includes a surface coating comprising the complexing material.

In some examples, the complexing substrate comprises a fabric.

In some examples, the fabric comprises cotton, linen, silk, hemp, bamboo, polyamides, polyesters, polyurethanes, or a combination thereof.

In some examples, the complexing substrate comprises a polymeric material.

In some examples, the polymeric material is a member selected from the group consisting of: polyvinyl alcohol, polyvinylpyrrolidone, carbomers, polyacrylic acid, polyoxyethylene/polyoxypropylene copolymers, other copolymers, albumins, casein, zein, collagen, other proteins, glucose, sucrose, maltose, trehalose, amylose, dextrose, fructose, mannose, galactose, other sugars, erythritol, threitol, arabitol, xylitol, ribitol, mannitol, sorbitol, galactitol, fucitol, iditol, inositol, volemitol, isomalt, maltitol, lactitol, maltotriitol, maltotetraitol, polyglycitol, other sugar alcohols, chondroitin and/or other glycosaminoglycans, inulin, starches, acacia gum, agar, carboxymethyl cellulose, methyl cellulose, ethyl cellulose, alginates, carrageenan, cassia gums, cellulose gums, chitin, chitosan, curdlan, gelatin, dextran, fibrin, fulcelleran, gellan gum, ghatti gum, guar gum, tragacanth, karaya gum, locust bean gum, pectin, starch, tara gum, xanthan gum, and other polysaccharides, and functionalized derivatives of any of the above, copolymers thereof, and combinations thereof.

In some examples, the complexing material comprises a native starch.

In some examples, the complexing material comprises a modified starch.

In some examples, the complexing substrate includes at least 0.75 nanograms (ng) complexing material/millimeter squared (mm$^2$) substrate surface area.

In some examples, the iodine layer comprises an iodine coating layer.

In some examples, the iodine coating layer comprises a binder, a filler, a plasticizer, a polymeric material, or a combination thereof.

In some examples, the moisture responsive film further includes a backing layer positioned on a back side of the complexing substrate opposite the side to which the iodine layer is applied.

In some examples, the moisture responsive film further includes a designated calibration area and a designated testing area.

In some examples, a method of manufacturing a moisture-responsive film can include:

combining a complexing material with a substrate material to prepare a complexing substrate that forms a visualizable complex in the presence of iodine and water; and applying a layer of iodine to the complexing substrate to form a moisture-responsive film.

In some examples, combining includes mixing or dispersing the complexing material throughout the substrate material.

In some examples, combining includes applying a complexing material coating to a surface of the substrate material to prepare the complexing substrate that forms a visualizable complex in the presence of iodine and water.

In some examples, applying the layer of iodine comprises coating a complexing surface of the complexing substrate with a non-aqueous iodine solution.

In some examples, applying the layer of iodine comprises direct condensation of iodine vapor to a complexing surface of the complexing substrate.

In some examples, applying the layer of iodine comprises coating a complexing surface of the substrate with an iodine coating layer.

In some examples, the iodine coating layer includes a binder, a filler, a plasticizer, a polymeric material, or a combination thereof.

In some examples, the method further includes applying a backing film to the substrate.

In some examples, the backing film is applied to the substrate material prior to combining the complexing material with the substrate material to prepare the complexing substrate.

In some examples, a method of detecting a moisture-related skin condition, can include:

providing a moisture-responsive film (MRF) as described herein to a subject;

applying a skin surface of the subject to the test area of the moisture-responsive film for a predetermined period of time;

removing the skin surface from the test area to reveal an exposed test area; and comparing the exposed test area to a calibration area to detect the presence or absence of the moisture-related skin condition.

In some examples, the skin surface is a foot surface, a hand surface, a face surface, a chest surface, an axillary surface, or a groin surface.

In some examples, the predetermined period of time is from 1 second to 300 seconds.

In some examples, the calibration area is included on the moisture-responsive film.

In some examples, the calibration area is included on a separate calibration strip.

In some examples, the calibration area is a digital calibration area that is not included on the moisture responsive film.

In some examples, the method further includes drying the skin surface prior to applying the skin surface of the subject to the test area.

In some examples, a moisture-responsive film (MRF) system, can include:

a moisture-responsive film (MRF) as described herein; and instructions directing an end user to apply the MRF to a surface for a predetermined period of time.

In some examples, the surface is a skin surface.

In some examples, the skin surface is a foot surface, a hand surface, a face surface, a chest surface, an axillary surface, or a groin surface.

In some examples, the predetermined period of time is from 1 second to 300 seconds.

In some examples, the MRF includes a calibration area.

In some examples, the calibration area is printed to prepare one or more calibration marks.

In some examples, the system further includes one or more water standards for application to the calibration area to prepare one or more calibration marks.

In some examples, the system further includes one or more calibration strips separate from the MRF.

In some examples, the system further includes a skin drying material.

In some examples, the skin drying material comprises a water-absorbent fabric, a paper-based towel, a disposable towelette including a drying solvent, or a combination thereof.

In some examples, the MRF comprises a plurality of test areas.

In some examples, a method of identifying surface features based on moisture content at the surface can include:

applying a surface to a test area of a moisture-responsive film (MRF) as described herein for a predetermined period of time; and removing the surface from the test area to reveal an exposed test area.

In some examples, the surface is a skin surface of a subject.

In some examples, the skin surface comprises a fingertip.

In some examples, the MRF comprises a plurality of test areas.

In some examples, applying the surface comprises applying individual fingertips of a subject to individual test areas of the plurality of test areas to obtain fingerprints of the subject.

In some examples, the method further includes comparing the exposed test area to a calibration area to detect the presence or absence surface features based on moisture content.

EXAMPLES

Example 1—Sweat Production Fingerprinting Using a Polyvinyl Alcohol Membrane Device The current inventors have developed a membrane-based adaptation of the iodine-starch complexation commonly used to visualize sweat pores, comprising a thin, flexible film of polyvinyl alcohol (PVA) and maltodextrin. In the presence of iodine, this film rapidly develops color when moistened. This film approach presents substantial advantages compared to the more common approach of using dry starch granules or granules dispersed in oil. The film shows coloration in high resolution, reflecting the homogeneous distribution of the starch in the dry membrane, and the coloration is developed within the film itself such that it can be removed from the underlying tissue substrate and subsequently visualized and permanently recorded (scanned) using standardized electronic methods, avoiding substantial visual analysis of spots seen on the irregular surface of the subjects' skin, and promoting quantitative comparisons of sweat levels.

In further detail, membranes prepared by drying polyvinyl alcohol/maltodextrin solutions are responsive to sweating in the presence of iodine. High-resolution images of sweat production with resolvable sweat ducts are produced by this "fingerprinting" method wherein an iodine coated skin surface is pressed against a dried starch/PVA film for several minutes. Areas as small as mouse paws and as large as human feet can be consistently assayed using this method and the resulting "films" can be stored in a dry environment or electronically imaged for more quantitative analysis.

The inventors have further adapted the membrane sensors described above to a paper-based device that does not require the use of PVA or any other separately applied polymer. Briefly, paper, fabric, or any other hydrophilic surface is loaded with a material known to form a colored complex in the presence of iodine and water, typically starch, maltodextrin or similar, although PVA may also be used in this role. The surface is dried, if necessary, and then elemental iodine is deposited onto this surface in an anhydrous fashion that precludes premature complexation. The resulting surface loaded with both iodine and a corresponding agent capable of forming a colored complex, is sensitive to water, rapidly developing a visible coloration upon exposure to minute quantities of water on the order of 150 $pL/mm^2$ or less, or 250 fL/pixel, or 1.8 pL of water exposure from an individual sweat pore. Iodine can be conveniently deposited in an anhydrous manner by direct vapor exposure from the crystalline solid, or by wetting of the starchy substrate by a solution of elemental material in an anhydrous (or nearly anhydrous) solvent such as reagent methanol or ethanol, or similar, followed by evaporative drying of the solvent, which proceeds more quickly than evaporative loss of iodine. The resulting films may be stored in a sealable container or package so as to preclude gradual loss of iodine content and must be stored in sufficiently low-humidity conditions to preclude condensation of liquid water and development of color in the film sensor material. Most commercial paper designed to accept printing includes so-called sizing-agents, imparting a number of benefits, which include uniform and ready absorption of ink materials. These sizing agents frequently include materials that, like starch, will form colored complexes with iodine in the presence of water, and thereby provide a ready platform adaptable to the moisture sensing devices described herein.

Example 2—Evaluation of Starch and Iodine Content in MRF

To evaluate the amount of starch and iodine required to visualize a color response to water, a non-starch loaded paper matrix, Kimwipe laboratory wipes (Kimberly-Clark, Irving, Tex.) were dosed with 1 µL spots of various solutions of maltodextrin as a model starch component. A 1 µL dose of a 0.01% wt. solution of maltodextrin in water formed a spot of approximately 8 mm in diameter, such that a starch deposition was accomplished of approximately 1 mg*0.01%/50 $mm^2$=0.000002 $mg/mm^2$=2 $ng/mm^2$. This dose reacted to form a colored region readily evident to visual inspection under ordinary light when treated with a similar quantity of anhydrous iodine solution and subsequently exposed to moisture. Lower starch levels of, for example, 500 $pg/mm^2$ did not form a visibly obvious and distinct signal in this exemplar embodiment of the system described herein.

Example 3—MRF in a Paper-Based Device

A sheet of standard ink-jet printer paper, such as Hammermill Inkjet Paper, product #105050 was exposed to approximately 0.5 g iodine vapor sublimed from a 50° C. plate into a 1 cubic foot volume for 1 hour at 20° C. ambient temperature. Upon removal, without further treatment, the resulting MRF shows strong sensitivity to contact with liquid water as from direct skin contact, although it may be readily manipulated in ambient 20° C., 55% humidity atmosphere without developing noticeable coloration.

Example 4—Calibration Characterization of a MRF

The MRF of Example 3 above is readily calibrated as to detection of specific moisture levels by application of minute quantities of water. Application of pure water results in a strongly visible deep purple coloration with a mean grayscale level of about 40, which is readily distinguished from the light tan background (non-wetted) level of about 220 on the standard 0-255 grayscale produced by scanning on a common flatbed color scanner, in this example an Epson Perfection V550 Photo Scanner (Epson America, Inc., Long Beach, Calif.), set to 1200 dpi 24-bit RGB scan parameters, the image analyzed using ImageJ open source image analysis software (http://imagej.nih.gov/ij, v. 1.50d). Similar relative gray levels and calculate response are found using a common cellphone camera (iPhone 7+, Apple Inc., Cupertino, Calif.), and the same software. A convenient method to deliver minute quantities of water is to introduce the water in the form of a solution in a non-aqueous solvent such as reagent ethanol or methanol. For example, when a 1 µL quantity of a 1% solution of water in dry acetone is applied to the MRF described in Example 2, a discernible color change in the paper results in the resulting spot, more than 10 gray levels or about 5% of the maximal color response, appearing over about 10 seconds as the acetone evaporates, leaving the water to soak into the MRF. This can provide a roughly circular spot about 4.5 mm in radius, or 4.5*600=2700 pixel widths in radius, with an area of about 63.6 mm$^2$, or 63.6*600=38000 pixels, about, in area. The spot thus visualized results from the 10 nL water content of the original 1 µL of solution, distributed over these 38000 pixels. Thus, color is apparent at a 1% water solution dose of 1 µL/38000 pixel, or a water dose of 10 pL/38000 pixel, or about 260 fL/pixel. The spot size observed as a colored region resulting from contact with an active human sweat pore is very readily observable by visual inspection of the scanned image, and can be as small as 0.12 mm in diameter, with an area of 0.011 mm$^2$. Thus the spot from a human pore can be over 5600-fold smaller in area than the 1 µL calibration spot size, corresponding to a water dose measured from the pore that is in the range of 10 nL/5600=1.7 pL. As such, quantitation of signal intensity in response to water exposure can be facilitated by delivery of precise volumes of water solutions of calibrated concentration, such that signal-response data is generated in-situ. Inclusion of one or more such calibration marks can serve to verify that the sensors are functional and may facilitate grading or quality control as well as providing a convenient read-out reference for subsequent use.

Figure 3A:
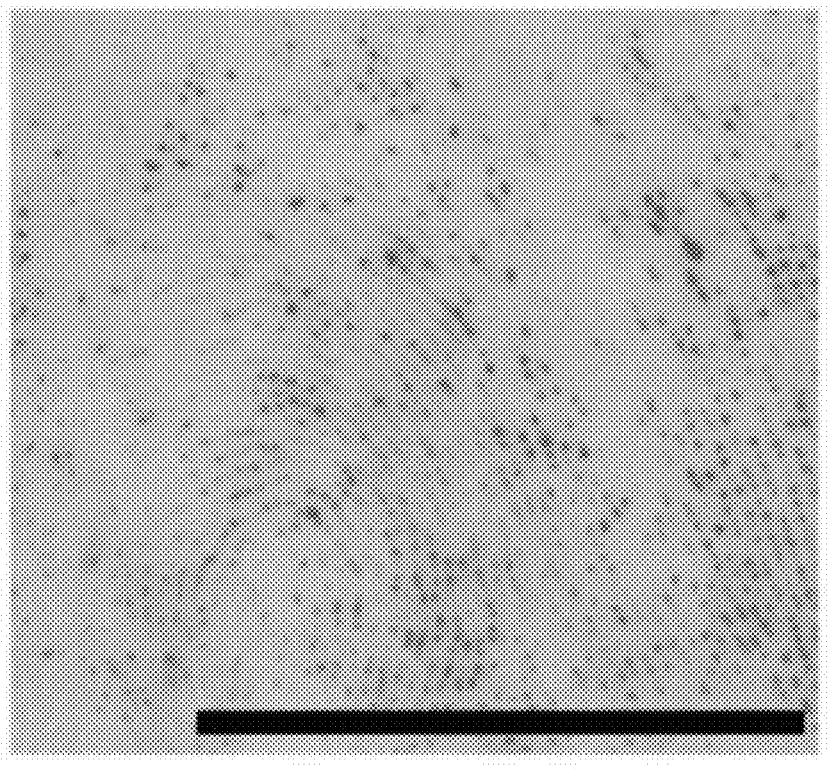
FIG. 3A depicts an MRF in accordance with examples of the present disclosure after 20 seconds of contact with palmar skin of a typical, non-hyperhidrotic sweat level, showing punctate dark spots corresponding to active sweat production at some pores.
Figure 3B:
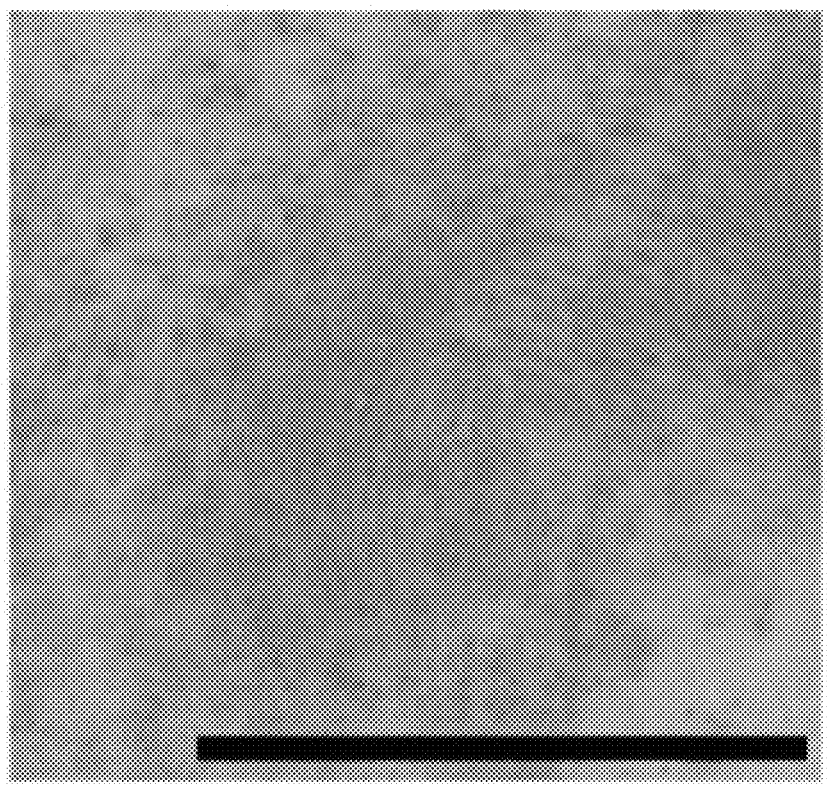
FIG. 3B depicts an MRF device in accordance with examples of the present disclosure after 20 seconds of contact with palmar skin having more active sweat production, which can be representative of mild hyperhidrosis.
Figure 3C:
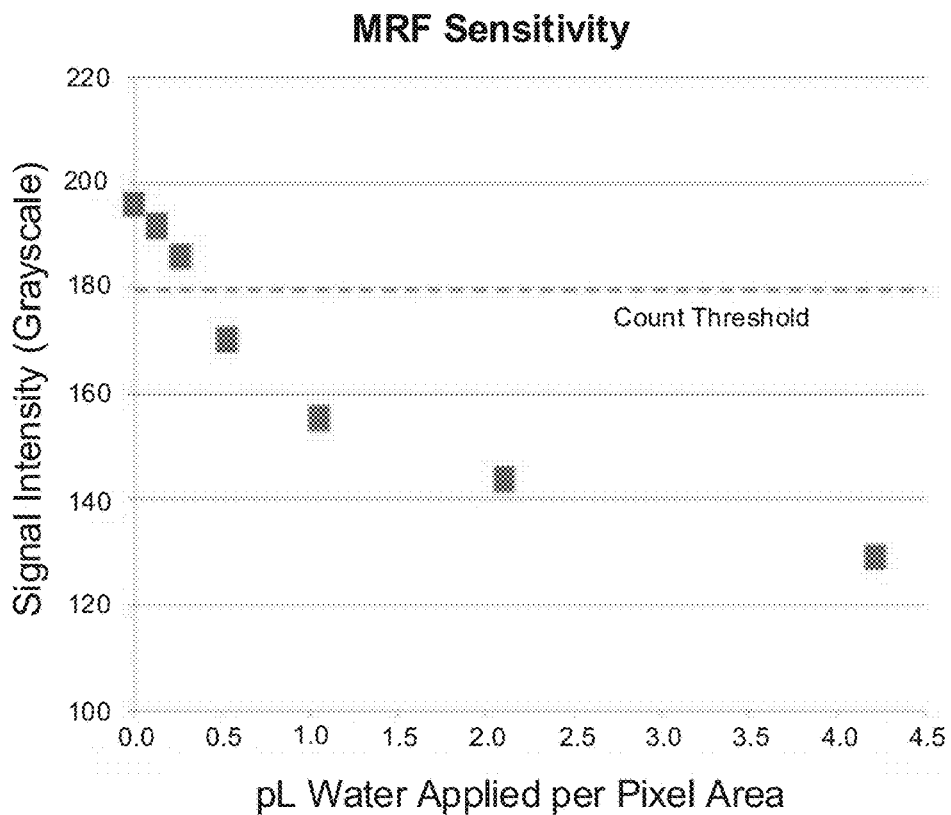
FIG. 3C illustrates an example of threshold detection of active glands for quantitative measurement.

For example, FIG. 3A presents an image of the paper-based MRF of Example 3 following a 20 second contact with human palmar skin showing well-defined, punctate dark spots arranged along the ridges of the epidermal skin where sweat pores made contact with the MRF, triggering the iodine-starch color reaction, similar to a dermatoglyph or fingerprint, but recording superficial sweat. This image depicts a MRF response to skin that might be considered within normal sweat range (individual not diagnosable with hyperhidrosis). FIG. 3B depicts a different region of the same sheet of paper following a similar 20 second contact with skin that might be considered to demonstrate some degree of hyperhidrosis (individual with this print might be diagnosable with hyperhidrosis). Scale bars denote ¾". As illustrated in FIG. 3B, punctate patterns similar to those observed in FIG. 1A are recorded, but in FIG. 3B these are in higher numbers and density than in the non-hyperhidrotic individual, as well as additional diffuse staining, possibly caused by wicking of excess moisture or from additional diffuse moisture at the surface of the epidermis. Such an image might form the basis of a diagnosis for hyperhidrosis through demonstration of total sweat output, distribution of sweating, or degree of wicking of excess sweat. Further, FIG. 3B or an expanded print of the whole hand might be used to identify specific areas with more or less hyperhidrosis, as a guide to subsequent treatment by a physician. Further, FIG. 3C presents response data from a set of calibrated 1 µL doses of selected water concentrations and the resulting response, with axes labeled to show the water dose on a per-pixel basis as well as the resulting gray level on the same paper-based MRF of Example 3 used to record the prints of FIG. 3A and FIG. 3B. It is noted that the y-axis charts the gray level of pixels where darkening due to water exposure shows as lower gray values, and the gray level of 195 seen for the 0.0 pL water dose reflects the non-darkened background gray level. The dotted line labeled "Threshold" illustrates an arbitrarily selected example of how a color threshold, in this case 180 gray, might be used to record water exposure above a preselected level, such as might be used to detect and count active glands or areas deemed hyperhidrotic for a quantitative measurement of sweating activity or density. Such a threshold number or numbers could be set in consultation with dermatologists to represent a useful diagnostic criterion for specific conditions such as hyperhidrosis, or other dysfunction of the sweat glands or ducts, or to gauge the action of a drug or therapy. Water response intensity was quantified by electronically imaging the film using an Epson Reflection V550 scanner run by Epson Scan software version 3.9.2.3US at 24-bit RGB color and 1200 dpi resolution settings. Images were saved as 1200 dpi images for analysis and image signal intensity levels were extracted using open-source ImageJ software version 2.0.0-rc-42/1.50d.

Analysis of images shown in FIG. 3A and FIG. 3B can be performed using a variety of methods, any of which may be suitable for determination of the degree of darkening of the MRF reflecting the quantity of moisture absorbed. For example, using a threshold value of gray value 180, which excludes the majority of the non-exposed area of the MRF (being a lighter tan color and scanning at a digital RGB gray value of 180 or higher) effectively delineates pixels corresponding to a roughly 250 fL or higher water dose on the corresponding area of the MRF. Using that threshold value, a count of pixels at lower gray values (darker pixels, indicating water exposure above threshold) tallies 295,313 pixels in FIG. 3A vs 1,394,286 pixels above threshold in FIG. 3B. Thus, the MRF signal arising from contact with the wetter skin of FIG. 3B is readily assigned a quantitative dark pixel count that is 1,394,286/295,313=4.7 fold higher than the less-wet skin of FIG. 3A. If dark pixels are not merely counted, but a weighted sum is used, being the sum of each pixel's inverted gray level (i.e. each pixel at a gray level of 60 sums as a value of 255−60=195, and so forth), the "score" thus produced for FIG. 1A is 2.63*10$^7$, while the wetter MRF of FIG. 3B scores at 1.40*10$^8$, thus enhancing the difference in wetness in the two scans, scoring about 5.3-fold higher in FIG. 3B as compared to FIG. 3A. As FIG. 3C shows, below about a 1 pL/pixel exposure level, the response of this example MRF is substantially linear and shows a 0.99+ correlation coefficient, making the use of a weighted sum reflective of a precise and quantitative measure of wetness over that range.

Figure 3D:
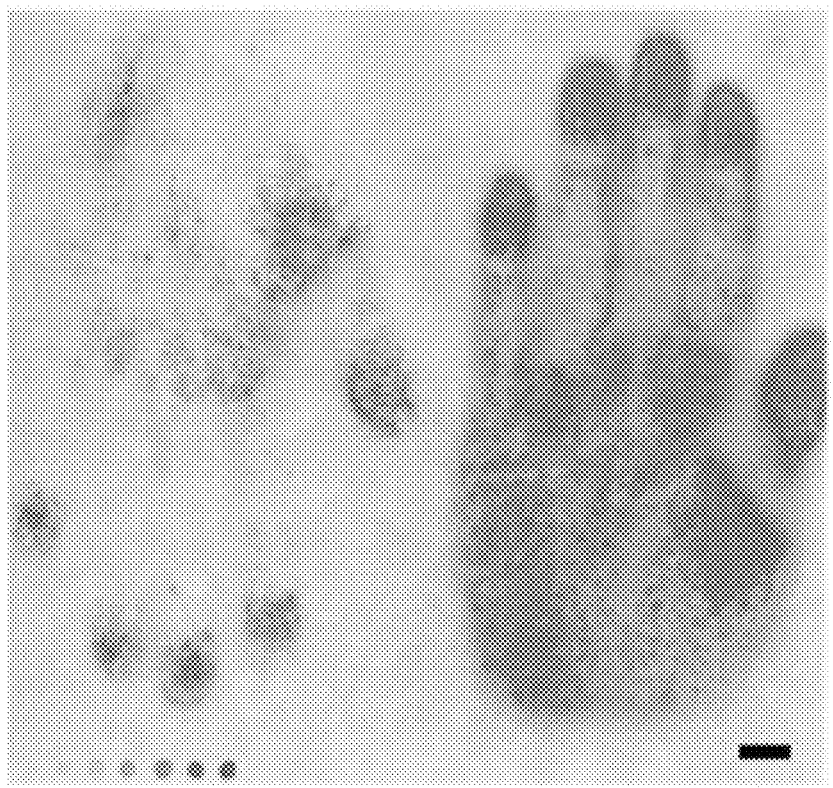
FIG. 3D depicts an MRF device in accordance with examples of the present disclosure that was used to record both hands sampled in FIG. 3A non-hyperhidrotic (right-hand side) and FIG. 3B potentially hyperhidrotic (left hand side), which are enlarged views of portions of FIG. 3D and a set of 1 µL calibration doses of varying water levels used to generate FIG. 3C (upper left region).

FIG. 3D depicts the single MRF sheet from which FIG. 3A, FIG. 3B, and FIG. 3C are extracted as sub-images. FIG. 3A shows an enlarged region taken from the non-hyperhidrotic full palm print at the left-hand side of FIG. 3D. FIG. 3B shows an enlarged region taken from the wetter, potentially hyperhidrotic full palm print at the right-hand side of FIG. 3D. At the lower left corner of FIG. 3D, a series of circular darkened regions are visible as calibrating marks resulting from application of 1 μL aliquots of a series of solutions of water in dry acetone, from which color intensity data were analyzed to produce the graph of FIG. 3C.

Figure 4A:
FIG. 4A illustrates a footprint showing capability of this approach to record sweat production over large areas (e.g., entire sole) in a single operation. The overlaid square shows the area enlarged for FIG. 2B, with scale bars of ¾".
Figure 4B:
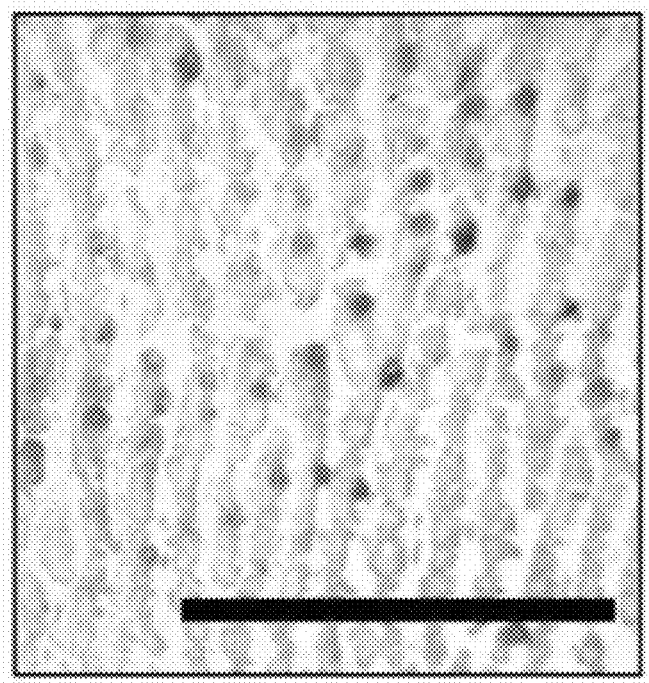
FIG. 4B illustrates a close-up view of detail recorded in the film, with individual pores readily discernable within skin ridges of plantar surface. Not all pores are active in this healthy volunteer, and light areas correspond to lack of contact of PVA film and dry sweat duct openings. Ridges are visible due to moisture content, although these are readily discerned versus the more intense coloration of the pores. Scale bar=500 µm.

FIG. 4A illustrates one specific example of a foot sweatprint acquired using a PVA-based MRF, demonstrating the capability of this approach to record sweat production over large areas (e.g., entire sole) in a single operation. Scale bars denote ¾", and the box shows the region enlarged in FIG. 4B. A close-up view of detail recorded in the film is illustrated in FIG. 4B, with individual pores readily discernable within skin ridges of the plantar surface. Not all pores are active in this healthy volunteer, and light areas correspond to lack of contact with the PVA film and dry sweat duct openings. Ridges are visible due to moisture content, although these are readily discerned versus the more intense coloration of the pores.

Figure 5:
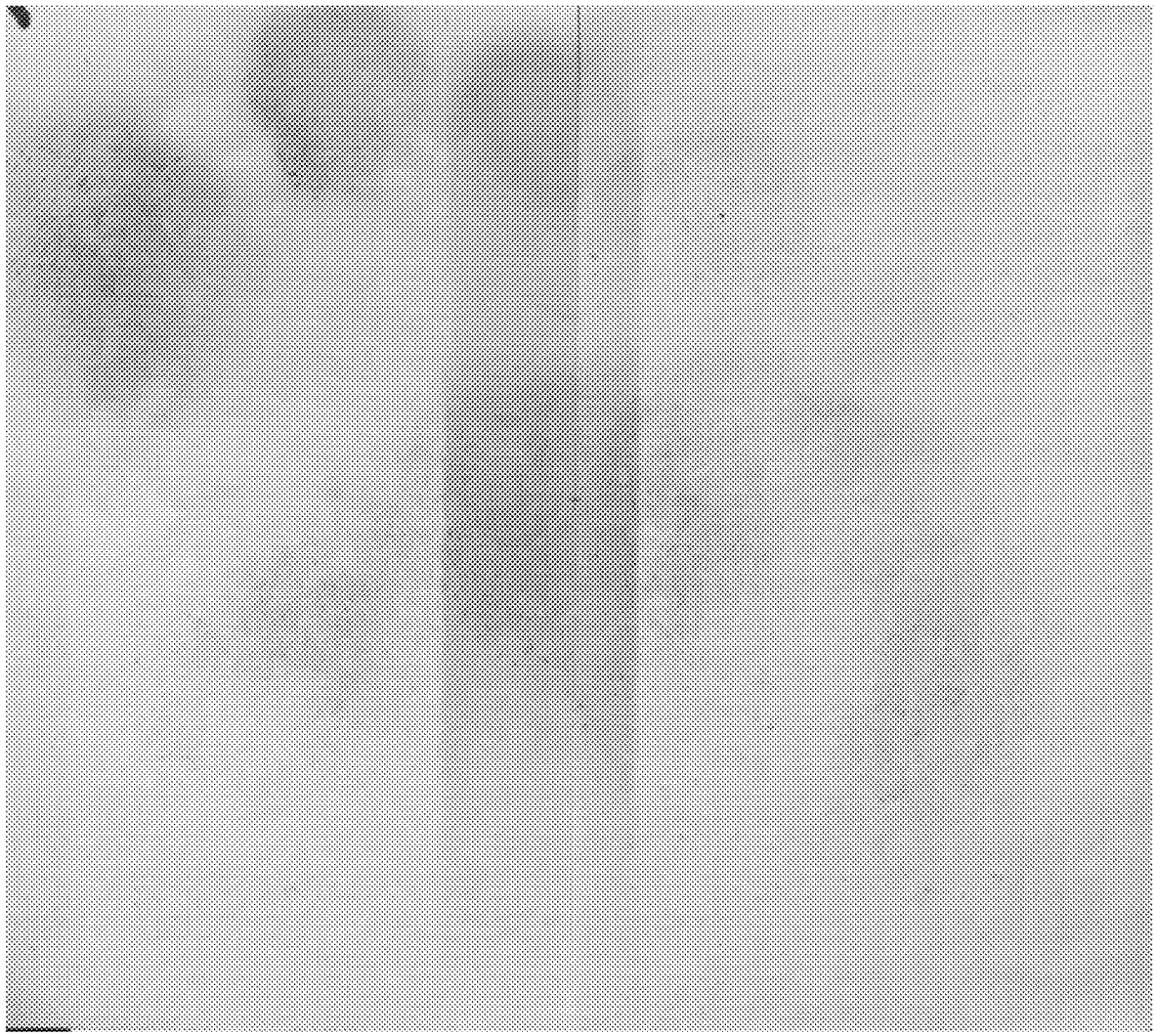
FIG. 5 illustrates two starch-containing films coupled together with an underlying strip of adhesive film that was affixed before moisture exposure. The film area overlying the adhesive film demonstrates increased sensitivity in detecting moisture content deposited by contact with a skin surface.

FIG. 5 illustrates two starch-containing paper-based films coupled together with an adhesive film on the back (non-exposed) surface. As can be seen in this image, the film backing can provide increased sensitivity in detecting moisture content on a skin surface.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed is:

1. A moisture-responsive film, comprising:
   a complexing substrate containing a complexing material that forms a visualizable complex in the presence of iodine and water; and
   an iodine layer applied to the complexing substrate to form a moisture-responsive film comprising a designated test area and a designated calibration area that form part of the iodine layer.

2. The moisture-responsive film of claim 1, wherein the complexing substrate comprises paper, fabric, a polymeric material, or a combination thereof.

3. The moisture-responsive film of claim 1, wherein the complexing substrate comprises paper.

4. The moisture-responsive film of claim 3, wherein the complexing material is mixed throughout the paper.

5. The moisture-responsive film of claim 3, wherein the paper includes a surface coating comprising the complexing material.

6. The moisture-responsive film of claim 1, wherein the complexing substrate comprises a fabric.

7. The moisture responsive film of claim 6, wherein the fabric comprises cotton, linen, silk, hemp, bamboo, polyamides, polyesters, polyurethanes, or a combination thereof.

8. The moisture-responsive film of claim 1, wherein the complexing substrate comprises a polymeric material.

9. The moisture-responsive film of claim 8, wherein the polymeric material is a member selected from the group consisting of: polyvinyl alcohol, polyvinylpyrrolidone, carbomers, polyacrylic acid, polyoxyethylene/polyoxypropylene copolymers, other copolymers, albumins, casein, zein, collagen, other proteins, glucose, sucrose, maltose, trehalose, amylose, dextrose, fructose, mannose, galactose, other sugars, erythritol, threitol, arabitol, xylitol, ribitol, mannitol, sorbitol, galactitol, fucitol, iditol, inositol, volemitol, isomalt, maltitol, lactitol, maltotriitol, maltotetraitol, polyglycitol, other sugar alcohols, chondroitin and/or other glycosaminoglycans, inulin, starches, acacia gum, agar, carboxymethyl cellulose, methyl cellulose, ethyl cellulose, alginates, carrageenan, cassia gums, cellulose gums, chitin, chitosan, curdlan, gelatin, dextran, fibrin, fulcelleran, gellan gum, ghatti gum, guar gum, tragacanth, karaya gum, locust bean gum, pectin, starch, tara gum, xanthan gum, and other polysaccharides, and functionalized derivatives of any of the above, copolymers thereof, and combinations thereof.

10. The moisture-responsive film of claim 1, wherein the complexing material comprises a native starch.

11. The moisture-responsive film of claim 1, wherein the complexing material comprises a modified starch.

12. The moisture-responsive film of claim 1, wherein the complexing substrate includes at least 0.75 nanograms (ng) complexing material/millimeter squared ($mm^2$) substrate surface area.

13. The moisture-responsive film of claim 1, wherein the iodine layer comprises an iodine coating layer.

14. The moisture-responsive film of claim 13, wherein the iodine coating layer comprises a binder, a filler, a plasticizer, a polymeric material, or a combination thereof.

15. The moisture-responsive film of claim 1, further comprising a backing layer positioned on a back side of the complexing substrate opposite the side to which the iodine layer is applied.

16. A method of detecting a moisture-related skin condition, comprising:
   providing a moisture-responsive film (MRF) according to claim 1 to a subject;
   applying a skin surface of the subject to the designated test area of the moisture-responsive film for a predetermined period of time;
   removing the skin surface from the designated test area to reveal an exposed test area; and
   comparing the exposed test area to the designated calibration area to detect the presence or absence of the moisture-related skin condition.

17. The method of claim 16, wherein the skin surface is a foot surface, a hand surface, a face surface, a chest surface, an axillary surface, or a groin surface.

18. The method of claim 16, wherein the predetermined period of time is from 1 second to 300 seconds.

19. The method of claim 16, further comprising drying the skin surface prior to applying the skin surface of the subject to the test area.

* * * * *